United States Patent [19]

Chabardes et al.

[11] Patent Number: 5,221,797
[45] Date of Patent: Jun. 22, 1993

[54] PROCESS FOR THE PURIFICATION OF PSEUDO-IONONE AND A COMPLEX FORMED DURING SAID PROCESS

[75] Inventors: Pierre Chabardes, Sainte Foy les Lyon; Noël Crenne, Lyons, both of France

[73] Assignee: Rhone-Poulenc Nutrition Animale, Commentry, France

[21] Appl. No.: 869,940

[22] Filed: Apr. 17, 1992

[30] Foreign Application Priority Data

Apr. 17, 1991 [FR] France ............................... 91 04711

[51] Int. Cl.$^5$ ........................... C07F 5/02; C07F 3/00; C07F 7/00; C07F 15/00
[52] U.S. Cl. ......................................... 556/7; 556/27; 556/42; 556/54; 556/57; 556/81; 556/130; 556/146; 556/182; 556/45; 568/1; 568/410; 568/414; 568/417
[58] Field of Search .................. 556/7, 27, 42, 54, 57, 556/81, 130, 146, 182, 45; 568/1, 410, 414, 417

[56] References Cited

U.S. PATENT DOCUMENTS 3,161,684 12/1964 Wilkinson et al. .................. 260/593

FOREIGN PATENT DOCUMENTS 807101 2/1959 United Kingdom .

Primary Examiner—José G. Dees
Assistant Examiner—Porfirio Nazario
Attorney, Agent, or Firm—Finnegan, Henderson, Farabow, Garrett & Dunner

[57] ABSTRACT

A process for the purification of pseudo-ionone, which comprises preparing pseudo-ionone by a reaction of citral with acetone, followed by bringing the reaction medium into contact with a metal derivative and thereafter distilling the pseudo-ionone.

12 Claims, No Drawings

PROCESS FOR THE PURIFICATION OF PSEUDO-IONONE AND A COMPLEX FORMED DURING SAID PROCESS

BACKGROUND OF THE INVENTION

The present invention relates to a new and novel process for for the purification of pseudo-ionone and to a chemical complex formed during the process.

Pseudo-ionone is prepared from citral and acetone by the following reaction:

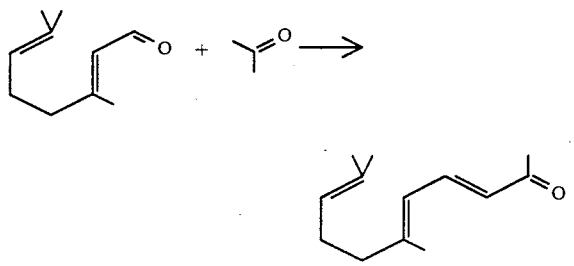

This reaction is generally carried out at a temperature of between 0° and 100° C. During the reaction, a by-product, shown as formula (I) below, is formed at the same time as the pseudo-ionone, because of an impurity in the citral, thereby resulting in a mixture of pseudo-ionone and formula (I), referred to herein as a pseudo-ionone mixture or as crude pseudo-ionone. This by-product is the condensation product of isocitral and acetone, which is formed according to the following reaction:

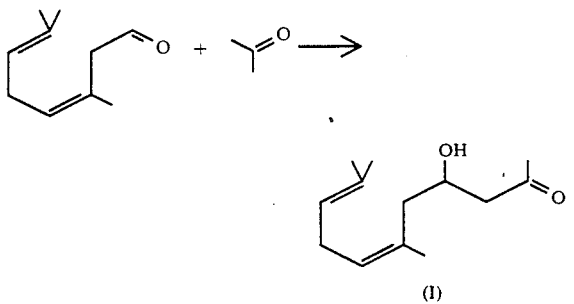

The by-product, i.e. condensation product formula (I), is more difficult to dehydrate than the aldol of citral, formed as an intermediate, which yields pseudo-ionone.

Moreover, condensation product formula (I) has a boiling point close to that of pseudo-ionone, and in order to separate these two compounds, it is necessary to use fractional distillation, which leads to a partial degradation of the pseudo-ionone. Accordingly, it would be desirable to provide a process of the preparation and isolation of pseudo-ionone wherein degradation of the pseudo-ionone is eliminated or substantially reduced.

SUMMARY OF THE INVENTION

In accordance with the present invention, a simple process has been discovered which makes it possible to eliminate the presence of the compound of formula (I) during the step of isolating pseudo-ionone.

The process of the present invention comprises heating a condensation mixture of citral and acetone containing the compound of formula (I) in the presence of a metal and/or boron derivative, and then distilling the pseudo-ionone from the mixture.

During this process, a complex is formed between the compound of formula (I) and the metal or boron. The complex is represented by the formula (II):

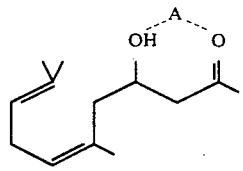

Unlike the compound of formula (I), the complex (II) can be separated from pseudo-ionone by distillation, thereby avoiding any noticeable degradation of the pseudo-ionone. In the complex (II), A represents boron or a metal atom. In a preferred embodiment, A represents an atom selected from magnesium, titanium, vanadium, chromium, nickel, zinc, boron, aluminum and lead. More preferably, A represents an atom selected from titanium, boron and magnesium.

DETAILED DESCRIPTION OF THE INVENTION

The metal and boron derivatives are preferably selected from:
magnesium derivatives such as magnesium acetate;
titanium derivatives such as isopropyl titanate;
vanadium derivatives such as triethanolamine orthovanadate;
chromium derivatives such as chromium acetate;
nickel derivatives such as nickel acetate;
zinc derivatives such as zinc acetate;
boron derivatives such as boric anhydride, boric acid, n-butyl borate and t-butyl borate;
aluminum derivatives such as aluminum isopropylate; and
lead derivatives such as lead acetate.

These derivatives are optionally employed in the presence of a tertiary amine.

Among the derivatives mentioned, it is preferable to use the titanium, boron and magnesium derivatives.

The reaction between the metal and/or boron derivative and the above-mentioned condensation mixture is preferably carried out at a temperature ranging from 50° to 150° C. The pressure used when the mixture and the metal and/or boron compound are brought into contact preferably ranges from 20 to 100 mm of mercury during distillation of the pseudo-ionone.

The amount of metal derivative and/or boron derivative is not critical as long as there is an amount sufficient to interact with or to complex with the compound of formula (I), thereby forming the complex of formula (II).

By this process, it is possible to remove at least 80% of the compound of formula (I) without any noticeable degradation of the pseudo-ionone.

EXAMPLES

The present invention will be described more fully by means of the examples which follow, which are not to be considered as limiting the invention. In the examples and throughout the specification and claims, all parts and percentages are by weight unless otherwise specified.

EXAMPLE 1

Crude pseudo-ionone was heated in the presence of t-butyl borate, in a proportion of 8.75 mol of borate per mole of the aldol of formula (I), from 25° C. to 105° C. for a period of 20 minutes and then for 45 minutes longer at 120°-130° C. under reduced pressure (100 mm of mercury; 13.3 kPa).

Analytical determinations showed that all of the aldol had disappeared and that 99.4% of the pseudo-ionone present in the crude product was recovered.

EXAMPLE 2

The procedure of Example 1 was repeated, except that t-butyl borate was replaced by boric acid in a proportion of 5.75 mol of boric acid per mole of the aldol of formula (I). The mixture was heated from 25° to 105° C. for a period of 35 minutes and then further heated for 2 hours and 10 minutes at 100°-110° C. under reduced pressure (100 mm of mercury: 13.3 kPa).

Analytical determinations showed that all of the aldol of formula (I) had disappeared and that all of the pseudo-ionone was recovered.

EXAMPLE 3

The procedure of Example 2 was repeated, except that the boric acid was replaced by boric anhydride in a proportion of 1.6 mol of boric anhydride per mole of the aldol of formula (I).

After 4 hours and 15 minutes of heating under reduced pressure (100 mm of mercury; 13.3 kPa), analytical determinations showed that all of the aldol of formula (I) had disappeared and that all of the pseudo-ionone was recovered.

EXAMPLE 4

Crude pseudo-ionone was heated for 30 minutes at 90° C. in the presence of isopropyl titanate in a proportion of 1.94 mol of isopropyl titanate per mole of the aldol of formula (I). Analytical determinations showed that all of the aldol of formula (I) had disappeared and that all of the pseudo-ionone was recovered.

EXAMPLES 5 TO 15

The procedure of Example 4 was repeated, except that crude pseudo-ionone was heated to 130° C. under reduced pressure (40 mm of mercury; 5.3 kPa) in the presence of each of the following different metal derivatives shown in the following table:

| Example No. | Metal derivative (MD) | MD/aldol (mol) | Period of heating | Aldol removed (%) | Pseudo-ionone degraded (%) |
|---|---|---|---|---|---|
| 5 | Al[OCH(CH$_3$)$_2$]$_3$ | 1 | 1 h 45 min | 80 | 3.6 |
| 6 | Triethanolamine titanate | 0.92 | 1 h 30 min | 90 | 4.6 |
| 7 | Ni(OCOCH$_3$)$_2$.4H$_2$O | 1.086 | 1 h 30 min | 84 | 0 |
| 8 | Zn(OCOCH$_3$)$_2$ | 1 | 1 h 30 min | 86 | 1.2 |
| 9 | Co(OCOCH$_3$)$_2$.4H$_2$O | 1.38 | 1 h 30 min | 87 | 0 |
| 10 | Cr(OCOCH$_3$)$_3$.2H$_2$O | 1.15 | 1 h 30 min | 85 | 0 |
| 11 | Mg(OCOCH$_3$)$_2$.2H$_2$O | 1.15 | 1 h 30 min | 100 | 0 |
| 12 | Mn(OCOCH$_3$)$_2$.4H$_2$O | 1.4 | 1 h 30 min | 100 | 4.9 |
| 13 | Pb(OCOCH$_3$)$_2$.3H$_2$O | 1.22 | 1 hr 30 min | 100 | 6 |
| 14 | Triethanolamine orthovanadate | 1.06 | 1 hr 30 min | 90 | 3.1 |
| 15 | — | — | 1 hr 30 min | 4 | 0 |

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A complex represented by the formula:

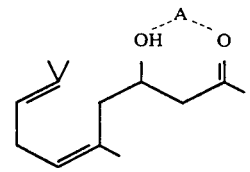

wherein A represents boron or a metal atom.

2. The complex of claim 1, wherein A represents an atom selected from cobalt, manganese, magnesium, titanium, vanadium, chromium, nickel, zinc, boron, aluminum and lead.

3. The complex of claim 1, wherein A represents an atom selected from titanium, boron and magnesium.

4. A process for the purification of pseudo-ionone, comprising contacting a pseudo-ionone mixture containing a compound of the Formula I

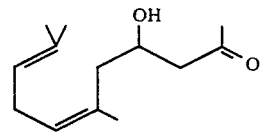

with a metal salt, a metal oxide, a boron derivative, or a mixture thereof, to form a complex of the Formula II

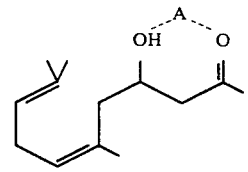

wherein A represents boron or a metal atom and thereafter distilling said pseudo-ionone.

5. The process of claim 4, wherein the pseudo-ionone is contacted with a derivative selected from cobalt, manganese, magnesium, titanium, vanadium, chromium, nickel, zinc, aluminum, lead and boron.

6. The process of claim 5, wherein the pseudo-ionone is contacted with a derivative of a metal selected from titanium and magnesium.

7. The process of claim 5, wherein the pseudo-ionone is contacted with a derivative of boron.

8. The process of claim 7, wherein the pseudo-ionone is contacted with tert-butyl borate.

9. The process of claim 4, further comprising adding a tertiary amine to said pseudo-ionone and metal derivative, boron derivative or mixture thereof.

10. The process of claim 4, wherein said contacting occurs at a temperature ranging from 50° to 150° C.

11. The process of claim 4, wherein said pseudo-ionone is distilled at a pressure ranging from 20 to 100 mm of mercury.

12. The process of claim 4, wherein said pseudo-ionone mixture is formed by the following reaction:

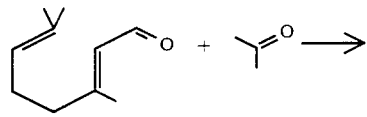

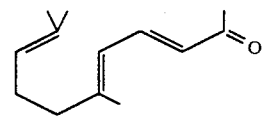

and wherein said pseudo-ionone compound of Formula (I) is simultaneously formed within said mixture as a condensation product of isocitral with acetone by the following reaction:

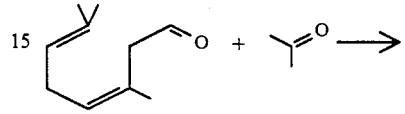

(I)

* * * * *